US00RE35004E

United States Patent [19]

Brois

[11] E Patent Number: Re. 35,004

[45] Reissued Date of Patent: Jul. 25, 1995

[54] CYCLIC CARBONYL CONTAINING POLYMERS

[75] Inventor: Stanley J. Brois, Westfield, N.J.

[73] Assignee: Exxon Research & Engineering Co., Florham Park, N.J.

[21] Appl. No.: 92,150

[22] Filed: Jul. 15, 1993

Related U.S. Patent Documents

Reissue of:

[64] Patent No.: 5,057,564
Issued: Oct. 15, 1991
Appl. No.: 556,243
Filed: Jul. 23, 1990

[51] Int. Cl.[6] ..... C08K 5/15; C07D 251/04

[52] U.S. Cl. ..... 524/101; 524/100; 525/333.7; 526/204; 526/269; 544/221

[58] Field of Search ..... 544/221; 526/204, 269; 525/333.7; 524/101

[56] References Cited

U.S. PATENT DOCUMENTS

| | | | |
|---|---|---|---|
| 2,945,836 | 7/1960 | Sacyer | 526/269 |
| 4,033,937 | 6/1977 | Argabright | 544/221 |
| 4,053,696 | 10/1977 | Herrle | 526/65 |
| 4,587,307 | 5/1986 | Bronstert | 525/333.7 |
| 4,824,906 | 4/1989 | Honsberg | 525/74 |
| 4,826,983 | 5/1989 | Neilan | 544/221 |
| 4,925,938 | 5/1990 | Neilan | 544/221 |

*Primary Examiner*—Fred Zitomer
*Attorney, Agent, or Firm*—Jay Simon

[57] ABSTRACT

The present invention relates to novel polymers which are adducts of an unsaturated hydrocarbon, wherein the novel polymers are produced by contacting cyclic carbonyl monomers with an unsaturated hydrocarbon to form novel cyclic carbonyl polymers having an Mn of about 500 to about $10^7$.

15 Claims, No Drawings

CYCLIC CARBONYL CONTAINING POLYMERS

Matter enclosed in heavy brackets [ ] appears in the original patent but forms no part of this reissue specification; matter printed in italics indicates the additions made by reissue.

FIELD OF THE INVENTION

The present invention relates to novel polymers which are adducts of cyclic carbonyl monomers or derivatives, with unsaturated organic molecules, wherein the novel products are produced by contacting cyclic carbonyl monomers with an unsaturated polymer to form the novel product. In particular the unsaturated polymer can be a polyolefin polymer ranging in molecular weight from about 500 to about 10,000,000.

The resultant adduct of cyclic carbonyl monomers and the unsaturated hydrocarbon polymer can be further reacted with: a polyamine, ammonia, amines or a nucleophilic reagent which can react with a carbonyl group including hydrides, Grignards, cyanohydrins, hydrazines, sulfites, phosphites, and hydroxylamines, and related reagents. The products are useful as solution viscosification agents.

BACKGROUND OF THE INVENTION

Various unsaturated hydrocarbon polymers have been reacted with maleic anhydrides to form a variety of maleic anhydride adducts of unsaturated hydrocarbon polymers. The reactivity of maleic anhydride with many unsaturated hydrocarbon polymers is poor and in some instances, as for example with EPDM rubber, even employment of extensive heating is ineffective. Free radical reactions which graft maleic anhydride onto the unsaturated hydrocarbon polymer have been utilized as alternative routes. Free radical grafting to chain scission, crosslinking and solvent grafting if the solvent is sufficiently reactive. The reaction of cyclic carbonyl monomers with the unsaturated hydrocarbon polymer overcomes these aforementioned deficiencies in that the cyclic carbonyl monomers can be reacted with the unsaturated hydrocarbon polymer at moderate temperatures in either the bulk or solution state without the employment of free radical initiators to form novel polymers which are useful as solution viscosifiers.

SUMMARY OF THE INVENTION

The present invention relates to novel polymers which are useful as solution viscosification agents. The novel polymers are produced by reacting a cyclic carbonyl monomer having ene-reactive carbonyl groups with an unsaturated hydrocarbon to form a novel cyclic carbonyl comaimg polymer having an Mn of about 500 to about $10^7$.

GENERAL DESCRIPTION

The present invention relates to novel polymers which are adducts of cyclic carbonyl monomers or derivatives, with unsaturated organic molecules, wherein the novel products are produced by contacting cyclic carbonyl monomers A and/or B with an unsaturated polymer to form the novel product. In particular the unsaturated polymer can be a polyolefin polymer ranging in molecular weight from about 500 to about 10,000,000.

The resultant adduct of cyclic carbonyl monomers and the unsaturated hydrocarbon polymer can be further reacted with: a polyamine, ammonia, amines or any nucleophilic agent that can react with a carbonyl group, such as hydrides, Grignards, cyanohydrins, hydrazines, sulfites, phosphites, and hydroxylamines, and related nucleophiles. The products are useful as solution viscosification agents.

Typical reactions to produce these novel cyclic carbonyl polymers are represented by the equations:

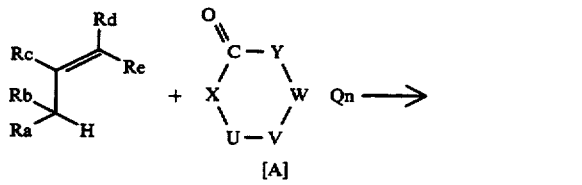

[A]

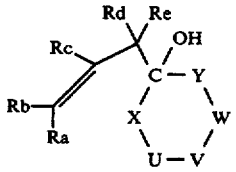

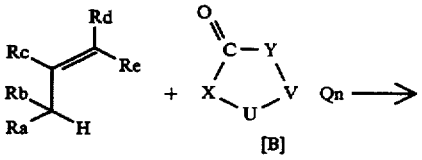

[B]

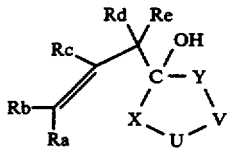

wherein Ra, Rb, Rc, Rd, and Re are independently selected from the group consisting of H, alkyl groups having about 1 to about $10^7$ carbon atoms, alkenyl groups having about 3 to about $10^7$ carbon atoms, wherein said alkyl and/or alkenyl groups can have one or more substituents selected from the groups consisting of alkoxy, aryloxy, Cl, CN, OH, acyl, aroyl, acyloxy, aryl, and $HO(CH_2CH_2)_x$ where $x=1-10$; $Q=H_2O$, MeOH, EtOH, n-BuOH or any suitable alcohol; $n=0.1$, $>1$; and X or Y are independently selected from the group consisting of $CH_2$, C═O, C═NOH; U, V and W are independently selected from the group consisting of $CH_2C$═O, C═NH, C═Nalkyl, wherein alkyl group has about 1 to about 18 carbon atoms; O, NH, Nalkyl, S, C═S, $CMe_2$, CH-phenyl, CH—CHOH—$CH_2OH$; $U+V=$1,2-phenylene, 1,8-naphthalene-diyl; 12-naphthalenediyl and 1,2-dihydroxyethylene-1,2-diyl.

Typical monomers include alloxan, indantrione, tetralintrione, dehydroascorbic acid, rhodizonic and croconic acid, triquinoyl, leuconic acid and keto-Meldrum's acid (A wherein $X=Y=C=O$, $U=W=O$ and $V=CMe_2$).

The acylic carbonyl monomer is reacted at about 20° C. to about 200° C. more preferably about 40° to 180° C. and most preferably about 60° to about 160° C.

Heating at about 100° C. under reflux conditions for about 4 to about 24 hours, preferably about 6 to about 18 hours, and most preferably about 8 to about 12 hours with an unsaturated hydrocarbon which is selected from the group consisting of EPDM terpolymers, EPR, polyisoprene, polybutadiene, 1-octadecene, Butyl rubber, styrene-butadiene and styrene-isoprene "random" and block copolymers, polybutenes, hydrocarbon resins such as a Escorez resins, etc. Oligomers or polymers which have olefin functionality near the end of the chain are of interest. Such molecules include, but are not limited to, octadecene, polyisobutene and polybutenes of various molecular weights, Vistanex, Vistanex J are examples of such polymers. Plastics such as polyethylene and polypropylene containing low levels of unsaturation are also suitable polyolefins.

Olefins substituted with functionality like CN, HO, $HO(CH_2CH_2)_x$ (x=1-10), alkoxy, Cl, and other groups illustrated below are useful reactants.

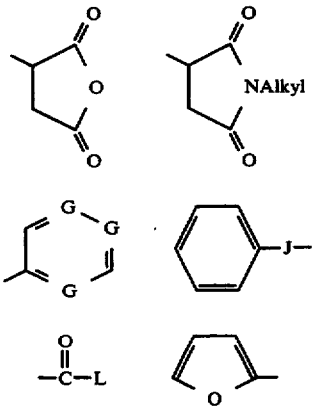

wherein G=C, N; J=O, S, $SO_2$; and and L is selected from the group consisting of OH; —$OR_1$; $NR_1R_2$; $R_1$; wherein $R_1$ has about 1 to about 18 carbon atoms,

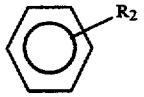

wherein $R_2$ is any alkyl and has about 1 to about 18 carbon atoms, —$NR_3R_4$ wherein $R_3$ and $R_4$ has about 1 or an alkyl group having about 1 to about 18 carbon atoms, —$COOR_6$ wherein $R_6$ is hydrogen or an alkyl group having about 1 to about 18 carbon atoms; and —$SR_7$, wherein $R_7$ is an alkyl group having about 1 to about 18 carbon atoms, Typical substituted olefins and polyolefins include oleic acid, linoleic acid, oleyl alcohol, methyl oleate, 2-octadecenyl succinic anthydride, octadecenyl benzene, 2-octadecenyl methyl ketone, 2-octadecenyl phenyl sulfide, 2-octadecenyl phenyl sulfone, octadecenyl chloride, polyisobutyenyl chloride, polyisobutenyl succmic anhydride, and related substituted olefins and polyolefins.

The expression "butyl rubber" as employed in the specification and claims, is intended to include copolymers made from a polymerization reaction mixture having thereto from 70 to 99.5% by weight of an isobutylene and about 0.5 to 30% by weight of a conjugated multiolefin having from about 4 to 14 carbon atoms, e.g., isoprene. The resulting copolymer contains 85 to 99.8% by weight of combined isoolefin and 0.2 to of combined multiolefin.

Butyl rubber generally has a Staudinger molecular weight as measured by GPC of about 20,000 to about 500,000, preferably about 25,000 to about 400,000 especially about 100,000 to about 400,000 and a Wijs Iodine No. of about 0.5 to 50, preferably 1 to 15. The preparation of butyl rubber is described in U.S. Pat. No. 2,356,128, which is incorporated herein by reference.

For the purposes of this invention, the butyl rubber may have incorporated thereto from about 0.2 to 10% of combined multiolefin; preferably about 0.5 to about 6% more preferably, about 1 to about 4%, e.g., 2%.

Illustrative of such a butyl rubber is Exxon butyl 365 (Exxon Chemical Co.), having a mole percent unsaturation of about 2.0% and a Mooney viscosity (ML, 1+3, 212° F.) of about 40 to 50.

Low molecular weight butyl rubbers, i.e., butyl rubbers having a viscosity average molecular weight of about 5,000 to 85,0000, and a mole percent unsaturation of about 1 to about 5%, may be sulfonated to produce the polymers useful in this invention. Preferably, these polymers have a viscosity average molecular weight of about 25,000 to about 60,000.

The EPDM terpolymers are low unsaturated polymers having about 0.5 to about 10.0 wt. % olefinic unsaturation, more preferably about 2 to about 8, most preferably about 3 to 7 defined accordingly to the definition as found in ASTM-1418-64 and is intended to mean terpolymers containing ethylene and propylene in the backbone and an olefin residue in the side chain as result of multi-olefin incorporation in the backbone. Illustrative methods for producing these terpolymers are found in U.S. Pat. No. 3,280,082, British Pat. No. 1,030,289 and French Pat. No. 1,386,600 which are incorporated herein by reference. The preferred polymers contain about 40 to about 75 wt. % ethylene and about 1 to about 10 wt. % of a diene monomer, the balance of the polymer being propylene. Preferably, the polymer contains about 45 to about 70 wt. % ethylene, e.g., 50 wt. % and about 2.6 to about 8.0 wt. % diene monomer, e.g., 5.0 wt. %. The diene monomer is preferably a nonconjugated diene.

Illustrative of these nonconjugated diene monomers which may be used in the terpolymer (EPDM) are 1,4-hexadiene, dicyclopentadiene, 5-ethylidene-2-norbornene, 5-methylene-2-norbornene, 5-propenylnorbornene, methyl tetrahydroindene and 4-methyl-5-methylene-2-norbornene.

A typical EPDM is Vistalon 2504 (Exxon Chemical Co.), a terpolymer having a Mooney viscosity (ML, 1+8, 212+ F.) of about 40 and having an ethylene content of about 50 wt. % and a 5-ethylidene-2-norbornene content of about 5.0 wt. %, The $M_n$ as measured by GPC of Vistalon 2504 is about 47,000, the $M_v$ as measured by GPC is about 145,000 and the $M_w$ as measured by GPC is about 174,000.

Another EPDM terpolymer Vistaion 2504-20 is is derived from Vistalon 2504 (Exxon Chemical Co.) by a controlled extrusion process, wherein the resultant Mooney viscosity at 212° F., is about 20. The $M_n$ as measured by GPC of Vistalon 2504-20 is about 26,000the $M_v$ as measured by GPC is about 90,000 and the $M_w$ as measured by GPC is about 125,000.

Nordel 1320 (Dupont) is another terpolymer having a Mooney viscosity at 212° F. of about 25 and having about 53 wt. % of ethylene, about 3.5 wt. % of 1,4-hexadiene, and about 43.5 wt. % of propylene).

The EPDM terpolymers of this invention has a number average molecular weight ($M_n$) as measured by GPC of about 10,000 to about 200,000, more preferably of about 15,000 to about 100,000, most preferably of about 20,000 to about 60,000. The Mooney viscosity (ML, 1+8, 212° F.) of the EPDM terpolymer is about 5 to about 60, more preferably about 10 to about 50, most preferably about 15 to about 40. The $M_n$ as measured by GPC of the EPDM terpolymer is preferably below about 350,000 and more preferably below about 300,000. The $M_w$ as measured by GPC of the EFDM terpolymer is preferably below about 500,000 and more preferably below about 350,000.

Other suitable olefin polymers include polymers comprising a major molar mount of $C_2$ to $C_5$ mono-olefins, e.g., ethylene, propylene, butylene, isobutylene and pentene. The polymers may be homopolymers such as polyisobutylene, as well as copolymers of two or more such olefins such as copolymers of ethylene and propylene, butylene and isobutylene, propylene and isobutylene and the like.

The reaction of the cyclic carbonyl monomer with the unsaturated hydrocarbon polymer can occur in solution, in a melt and in polymer processing equipment such as a rubber mill, a Brabender, an extruder or a Banbury mixer.

Typically, the polymer is dissolved in a suitable solvent, such as tetrahydrofuran, xylene or mineral oil and heated to temperatures ranging from about 40° C. to about 140° C. The cyclic carbonyl monomer, as a hydrate or hemiketal of methanol or butanol or some suitable alcohol, is dissolved in a suitable solvent such as tetrahydrofuran, dioxane, butanol or a suitable alcohol, and added gradually to the heated polymer solution.

The reaction mixture is heated, with stirring, until infrared and/or NMR analysis of the mixture indicates that the ene-addition of the carbonyl monomer to the unsaturated polymer is complete. Depending on temperature and concentration, reaction periods of about 4 to 40 hours are sufficient to achieve high conversion to ene adducts.

Bulk reactions can be carried out at about 40° C. to about 200° C. for approximately 3 to 300 minutes depending upon polyolefin and carbonyl monomer reactivity.

If necessary, products can be isolated by solvent removal by evaporation, or by adding the reaction mixture to a polar solvent such as acetone, which induces the precipitation of the functionalized polymer.

If desired, ene additions of cyclic carbonyl monomers to unsaturated hydrocarbon polymers can be effected in the presence of acid catalysts selected from the group consisting of kaolin, montmorillonite, silicates, $SnCl_4$, $AlCl_3FeCl_3$and $BF_3$.

Typically, 0.1 to 1 gram of acid catalyst per 0.01 to 1.0 moles of reactants would be employed.

DESCRIPTION OF THE PREFERRED EMBODIMENTS

The following examples illustrate the present invention without, however, limiting the same hereto.

EXAMPLE 1

Fifty millimoles (12.5 grams) of 1-octadecene dissolved in 12.5 grams of 1,4-dioxane were heated in a magnetically stirred, nitrogen blanketed reactor fitted with a reflux condenser and a thermometer. To the refluxing (ca. 102° C.) solution was gradually added fifty millimoles (0.8 grams) of alloxan hydrate dissolved in 80 mi of dioxane. After the addition of alloxan, the mixture was refitted for about six hours. After standing overnight at room temperature, the reaction solution turned into a solid crystalline mass which, upon heating, redissolved in dioxane. The reaction mixture was heated to about 130° C. for about 8 hours, and then cooled overnight. The crystals that separated from solution were filtered off, and subsequently recrystallized from dioxane. The dried crystals melted at 102°-104° C. and analyzed for 64.32% C, 9.38% H, and 6.80% N. Theory for the monohydrate of the ene adduct requires 64.07% C, 9.71% H. and 6.80% N. The crystalline product featured an infrared spectrum with intense twin carbonyl absorptions at about 5.85 and 5.92 microns, a carbon magnetic resonance spectrum with characteristic sp2 carbon signals at about 170.3, 148.3, 138.3 and 119.5 ppm, and a CI mass spectrum with a protonated molecular ion at mass 395, confirming the molecular weight of 394 for the ene adduct. These data are consistent with the structure shown below:

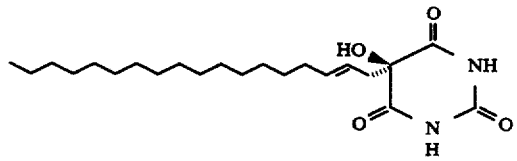

In a similar manner, alloxan was successfully ene-added to ethyiidene norbornene, and 2,4,4-methyl-2-pentene. The use of excess alloxan under forcing conditions, i.e., longer reaction times, and higher temperatures, caused multiple additions of alloxan to the olefin reactant, thus providing an ene route to di- and polyalloxan substituted olefins and polyolefins.

EXAMPLE 2

Ten grams of hot polyisobutylene, Mn=950, was poured into a nitrogen blanketed reactor fitted with a mechanical stirrer, thermometer, and condenser. The polyisobutylene was heated to about 150° C. in an oil bath, and 1.6 grams of alloxan monohydrate dissolved in 20 ml of dioxane, was added dropwise to the stirred polymer over a four hour period. Heating the reaction mixture at 150° C. was continued for about ten hours. When cool, the residue was drooled in about 100 ml of cyclohexane, filtered through Celite, and concentrated by sparging with nitrogen overnight. The residue analyzed for 1.84% N, and featured an infrared spectrum with a dominant carbonyl absorption band at about 5.85 microns. UV-GPC analysis showed that the polyisobutylene polymer was uniformly substituted with alloxan, and the MW distribution of the polyisobutylene were unaffected by ene-modification.

EXAMPLE 3

Ten grams of poly co-ethylene propylene ethylidene norbornene terpolymer, Mn=55,000, containing about 43 wt. % propylene, and 5 wt. % ethylidene norbornene, was dissolved in 90 grams of xylene, and poured into a nitrogen blanketed reactor fitted with a mechanical stirrer, and reflux condensor.

Using a silicone oil bath, the reactor was heated to 120° C. and 0.5 gram of alloxan hydrate dissolved in 30 ml dioxane was added all at once to the xylene solution of the terpolymer. The reaction mixture was stirred at 120° C. for about eight hours. The functionalized polymer was precipitated by addition of the cooled reaction mixture to a liter of acetone. The dried polymer analyzed for 0.76% N, and featured an infrared spectrum (film) with an intense carbonyl absorption band at about 5.9 microns. GPC analysis showed that ene functionalization with alloxan, in contrast with conventional free radical processes, did not affect the MW distribution of the terpolymer.

EXAMPLE 4

Fifty millimoles (8.9 grams) of ninhydrin hydrate dissolved in 30 ml of 1,4-dioxane, and 16 ml of 1-octadecene were successively added to a nitrogen blanketed 100 ml reactor fitted with reflux condenser, thermometer, and magnetic stirrer. The reaction mixture was heated at reflux (ca. 102° C.) in an oil bath for about 13.5 hours, and then transferred into an Erlenmeyer flask for refrigeration. The white precipitate that separated from solution was filtered, and recrystallized from dioxane. The dried powder melted at 68°-72° C., and analyzed for 79.48% C, and 10.56% H. Theory requires 78.64% C, and 9.71% H. The recrystallized product featured an infrared spectrum with a strong hydroxyl absorption band at 3.0 microns, and a dominant pair of carbonyl absorption bands at 5.8 and 5.9 microns; and a carbon magnetic resonance spectrum with characteristic carbonyl, aromatic, and olefinic carbon signals consistent with structure shown below:

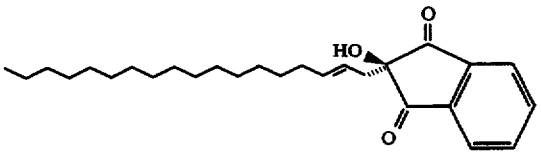

High yields of ene adducts of ninhydrin and dehydroascorbic acid with ethylidene norbornene, and 2,2,4-trimethyl-2-pentene were also realized in reactions conducted in refluxing 1,4-dioxane and and butanol. The ene adducts of indantrione (ninhydrin) with olefins were readily amenable to reactions with amines, and other nucleophilic reagents.

EXAMPLE 5

Ten grams of polyisobutylene, MW=950, and two grams of indantrione hydrate were combined in a nitrogen blanketed reactor fitted with a mechanical stirrer and condenser. The stirred mixture was heated in an oil bath at 140°-150° C. for about 28 hours, then cooled, and dissolved in 100 ml of cyclohexane. The mixture was filtered through Celite, and concentrated by evaporation using a stream of nitrogen. The residue analyzed for 3.96% O, and featured an infrared spectrum with an intense carbonyl absorption band at about 5.9 microns.

EXAMPLE 6

Ten grams of poly co-ethylene propylene ethylidene norbornene terpolymer, Mn=55,00 with 43% propylene and 5% ethylidene norbornene, were dissolved in 90 grams of xylene and charged into a nitrogen blanketed reactor equipped with a mechanical stirrer and condenser. The stirred mixture was heated to about 120° C. in an oil bath, and then 0.5 gram of indantrione hydrate dissolved in 30 ml of 1,4-dioxane was added in one portion to the reactor. The reaction mixture was kept at 120° C. for about six hours, then cooled, and a 10 ml portion added to 100 ml of acetone. The precipitated polymer was washed with acetone, and dried under high vacuum at about 40° C. The modified polymer analyzed for 1.74% O, and featured an infrared spectrum dominated by an intense carbonyl absorption at about 5.9 microns.

In a similar manner, terpolymer modification with indantrione was also effected in other solvents such as tetrahydrofuran.

What is claimed is:

1. An adduct of a substituted or unsubstituted, unsaturated olefinic or polymeric hydrocarbon and a cyclic, ene-reactive carbonyl-containing monomer, said adduct having a number average molecular weight in the range of about 500 to 10,000,000, said adduct [prepared by heating a mixture] *comprising the reaction product* of said unsaturated hydrocarbon and a cyclic, ene-reactive carbonyl-containing monomer characterized by the structures A, B or mixtures of A and B:

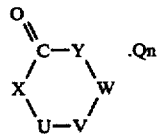

[A]

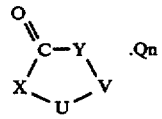

[B]

wherein Q is selected from the group consisting of $H_2O$, MeOH, EtOH, and BuOH; n is 0, 1 or greater than 1; X and Y are independently selected from the group consisting of $CH_2$, C=O and C=NOH; U, V and W are independently selected from the group consisting $CH_2$, C=O, C=NH, C=N-alkyl, O, NH, N-alkyl, S, C-=S, $CMe_2$, CH-phenyl and [CHCHOH—$CH_0$OH], *CHCHOH—$CH_2$OH* wherein said alkyl group has from 1 to about 18 carbon atoms; and wherein U+V may be 1,2-phenylene, 1,8-naphthalene-diyl, and 1,2-dihydroxyethylene-1,2-diyl.

2. The adduct of claim 1 wherein said unsaturated hydrocarbon is an olefin.

3. The adduct according to claim 2 wherein said olefin contains substituents selected from the group consisting of CN, HO, $HO(CH_2CH_2O)_x$, wherein (x=1-10), alkoxy, Cl, and

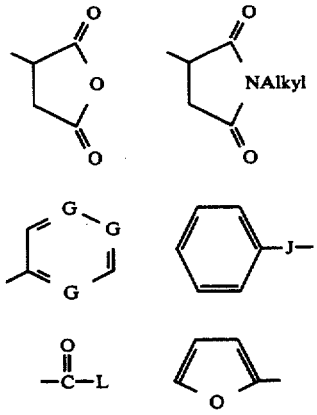

wherein G=C, N; J=O, S, $SO_2$; and and L is selected from the group consisting of OH; —$OR_1$, $NR_1R_2$; wherein $R_1$ about 1 to about 18 carbon atoms.

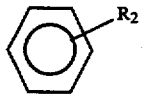

wherein $R_2$ is any alkyl and has about 1 to about 18 carbon atoms, —$NR_3R_4$ wherein $R_3$ and and $R_4$ has about 1 to about 18 carbon atoms, $OR_5$ wherein $R_5$ is hydrogen or an alkyl group having about 1 to about 18 carbon atoms, —$COOR_6$ wherein $R_6$ is hydrogen or an alkyl group having about 1 to about 18 carbon atoms, and —$SR_7$, wherein $R_7$ is an alkyl group having about 1 to about 18 carbon atoms.

4. The adduct of claim 1 wherein said olefin is 1-octadecene.

5. The adduct of claim 1 wherein said unsaturated hydrocarbon is a polymer selected from the group consisting of polyethylene, polypropylene, ethylene/propylene copolymers, ethylene/propylene/diene terpolymers, polyisoprene, polybutadiene, butyl rubber, styrene-butadiene and styrene-isoprene random or block copolymers, polybutenes and polyisobutylene.

6. The adduct of claim 5 wherein said polymer is polyisobutylene.

7. The adduct of claim 5 wherein said polymer is a terpolymer of ethylene, propylene and diene.

8. The adduct of claim 7 wherein said diene is ethylidene norbornene.

9. The adduct of claim 1 wherein said carbonyl-containing monomer is selected from the group consisting of alloxan, indantrione, tetralintrione, dehydroascorbic acid, rhodizonic acid, croconic acid, triquinoyl, [leuconcic] *leuconic* acid and keto-Meldrum's acid.

10. The adduct of claim 9 wherein said carbonyl-containing [member] *monomer* is alloxan.

11. The adduct of claim 1 prepared by heating [said] *a* mixture *comprising said hydrocarbon and said monomer* at a temperature in the range of abut 40° to about 140° C.

12. The adduct of claim 1 prepared by heating a solution of [said] *a* mixture *comprising said hydrocarbon and said monomer* in organic solvent at a temperature in the range of about 40° to about 140° C.

13. The adduct of claim 12 wherein said heating is conducted for a period of from about 4 to about 40 hours.

14. The adduct of claim 11 wherein said heating is conducted in the presence of an acid catalyst.

15. A process for preparing the adduct of claim 1 comprising [heating a mixture of] *contacting* said unsaturated hydrocarbon and said cyclic, ene-reactive carbonyl-containing monomer at a temperature [in the range of from about 40° C.] *of about 20° C.* for a period of time sufficient to form said adduct.

* * * * *

UNITED STATES PATENT AND TRADEMARK OFFICE

CERTIFICATE OF CORRECTION

PATENT NO. : RE, 35,004

DATED : July 25, 1995

INVENTOR(S) : Stanley J. Brois

It is certified that error appears in the above-indentified patent and that said Letters Patent is hereby corrected as shown below:

Column 8, claim 1, line 36 "$CHCHOH\text{-}CH_0OH$" should read --$CHCHOH\text{-}CH_2OH$--.

Signed and Sealed this

Twenty-eighth Day of November 1995

*Attest:*

Bruce Lehman

BRUCE LEHMAN

*Attesting Officer*

*Commissioner of Patents and Trademarks*